US 6,585,229 B2

(12) United States Patent
Cote, Sr. et al.

(10) Patent No.: US 6,585,229 B2
(45) Date of Patent: *Jul. 1, 2003

(54) MEDICAL NOZZLE SECURING APPARATUS

(75) Inventors: Andrew L. Cote, Sr., Merrimack, NH (US); Brian L. Newton, Woonsocket, RI (US); Charles F. Ganem, Neddick, ME (US)

(73) Assignee: Nypro Inc., Clinton, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/437,878
(22) Filed: Nov. 10, 1999

(65) Prior Publication Data

US 2001/0042850 A1 Nov. 22, 2001

Related U.S. Application Data

(60) Provisional application No. 60/117,583, filed on Jan. 27, 1999.

(51) Int. Cl.⁷ ............................................. A61M 25/16
(52) U.S. Cl. ...................... 251/149.1; 604/905; 604/249
(58) Field of Search ........................ 251/149.1, 149.4, 251/149.6, 149.7; 604/256, 905, 246, 249, 167.01, 167.02, 167.03, 167.06, 240, 243; 285/9.2

(56) References Cited

U.S. PATENT DOCUMENTS

| 4,143,853 A | 3/1979 | Abramson | 251/149.1 |
|---|---|---|---|
| 4,589,871 A | * 5/1986 | Imbert | 604/240 |
| 4,696,326 A | * 9/1987 | Sturgis | 251/149.6 X |
| 5,129,891 A | * 7/1992 | Young | 604/905 X |
| 5,171,234 A | 12/1992 | Jepson et al. | 604/283 |
| 5,222,948 A | 6/1993 | Austin et al. | 604/213 |
| 5,242,393 A | 9/1993 | Brimhall et al. | 604/86 |
| 5,263,945 A | 11/1993 | Byrnes et al. | 604/283 |
| 5,279,571 A | 1/1994 | Larkin | 604/167 |
| 5,295,657 A | 3/1994 | Atkinson | 251/149.1 |
| 5,454,409 A | 10/1995 | McAffer et al. | 141/329 |
| 5,470,319 A | 11/1995 | Mayer | 604/167 |
| 5,501,426 A | 3/1996 | Atkinson et al. | 251/149.1 |
| 5,533,708 A | 7/1996 | Atkinson et al. | 251/149.1 |
| 5,616,130 A | 4/1997 | Mayer | 604/167 |
| 5,669,881 A | 9/1997 | Dunshee | 604/164 |
| 5,674,206 A | 10/1997 | Allton et al. | 604/249 |
| 5,806,831 A | * 9/1998 | Paradis | 251/149.1 |
| 5,851,201 A | * 12/1998 | Ritger et al. | 604/240 |
| 5,957,898 A | * 9/1999 | Jepson et al. | 604/256 |
| 6,039,302 A | * 3/2000 | Cote, Sr. et al. | 251/149.1 |
| 6,165,168 A | * 12/2000 | Russo | 604/256 X |

* cited by examiner

*Primary Examiner*—Ehud Gartenberg
*Assistant Examiner*—Eric Keasel
(74) *Attorney, Agent, or Firm*—Bromberg & Sunstein LLP

(57) ABSTRACT

A medical coupling device manufactured from a device material provides an secure friction fit to a male nozzle device. To that end, the medical coupling device includes a fluid port (with an inner periphery) for receiving a male nozzle with a nozzle outer diameter, and a coupling material having a coupling material frictional value that is greater than the device material frictional value. The coupling material preferably is disposed about the inner periphery of the fluid port, while it and the inner periphery form an opening having an opening inner diameter. The opening inner diameter preferably is sized to receive and secure the male nozzle. The device material frictional value preferably is lower than the coupling material frictional value.

12 Claims, 3 Drawing Sheets

MEDICAL NOZZLE SECURING APPARATUS

PRIORITY

This patent application claims priority from U.S. provisional patent application entitled "MEDICAL NOZZLE SECURING APPARATUS," identified by U.S. Ser. No. 60/117,583, filed Jan. 27, 1999 the disclosure of which is incorporated herein, in its entirety, by reference.

FIELD OF THE INVENTION

The invention generally relates to medical products and, more particularly, the invention relates to devices for securing a medical nozzle within a mating female port of a medical valving device.

BACKGROUND OF THE INVENTION

Male luer devices commonly are inserted into female ports of valving devices for transferring fluids to or from a patient. For example, as shown in U.S. Pat. No. 5,295,657 (Atkinson), a blunt male luer tip may be inserted into an input port of a valved medical coupling device ("valve") to transfer medicament and/or other fluids to or from a patient. In a manner similar to that shown in the Atkinson disclosure, many male luer tips include a securing collar that mates with threads on the valve to secure the luer tip to the valve. Use of such a securing collar, however, increases the cost of such tips, while also requiring additional time to couple with the valve.

Other male luer tips, however, do not include a securing collar (e.g., luer slips). Accordingly, such male luer tips often are not securely coupled with the valve and consequently, become dislodged during use. In addition to being a medical hazard, such luer dislodging often disrupts the fluid transfer process.

SUMMARY OF THE INVENTION

In accordance with one aspect of the invention, a medical coupling device manufactured from a device material provides a secure friction fit to a male nozzle device. To that end, the medical coupling device includes a fluid port (with an inner periphery) for receiving a male nozzle with a nozzle outer diameter, and a coupling material having a coupling material frictional value that is greater than the device material frictional value. The coupling material preferably is disposed about the inner periphery of the fluid port, while it and the inner periphery form an opening having an opening inner diameter. The opening inner diameter preferably is sized to receive and secure the male nozzle. The device material frictional value preferably is lower than the coupling material frictional value.

In preferred embodiments, the opening inner diameter is no more than about two percent smaller than the nozzle outer diameter. In other embodiments, the nozzle is a standard male luer. The coupling material may be in the form of an annular ring, or one or more strips.

The coupling material may be comprised of elastomeric material, rubber, or other material having a friction that is higher than that of the device material. The coupling material may have a distal end that is fixedly secured to the inner periphery. In alternative embodiments, the male nozzle includes an outer periphery having a gripping material disposed thereabout. The gripping material may be disposed about either one of the male nozzle, or the medical coupling device.

In accordance with another aspect of the invention, a medical coupling device manufactured from a device material having a device material frictional value includes a male fluid port having an outer periphery, and a coupling material disposed about the outer periphery of the male fluid port. The coupling material preferably has a coupling material frictional value that is greater than the device material frictional value.

In accordance with another aspect of the invention, a medical coupling device manufactured from a device material having a device material frictional value includes a proximal fluid port for receiving a male nozzle with a nozzle outer diameter, a plunger valve for valving fluid flow through the proximal fluid port, and coupling material having a coupling material frictional value that is greater than the device material frictional value. The proximal fluid port has an inner periphery and is disposed about the inner periphery of the fluid port. In preferred embodiments, the coupling material and inner periphery form an opening having an opening inner diameter that receives the plunger valve. The opening inner diameter is sized to receive and secure the male nozzle. When coupled with the proximal fluid port, the nozzle remains proximal to the plunger valve.

BRIEF DESCRIPTION OF THE DRAWINGS

The foregoing and other objects and advantages of the invention will be appreciated more fully from the following further description thereof with reference to the accompanying drawings wherein.

DESCRIPTION OF PREFERRED EMBODIMENTS

Figure 1:
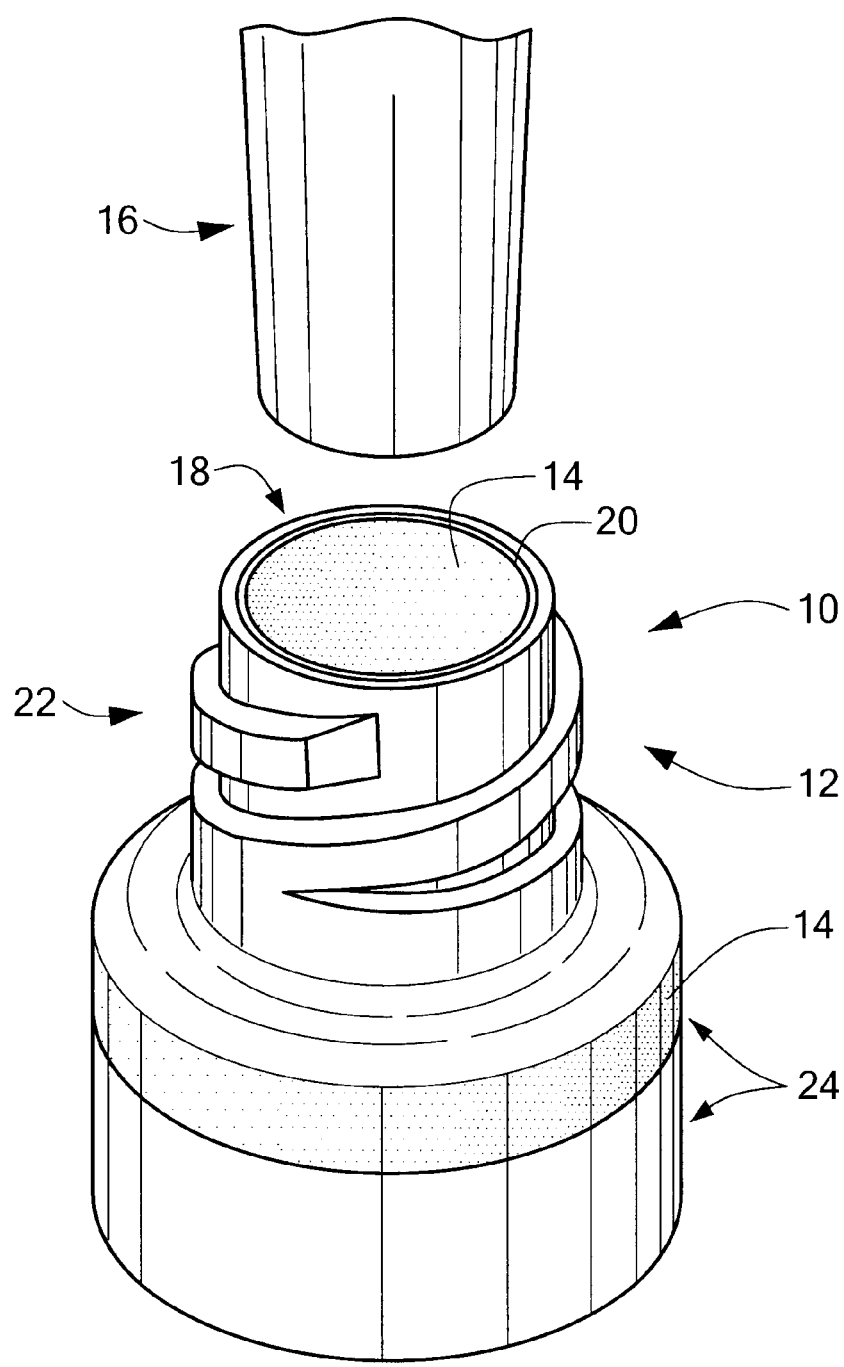
FIG. 1 schematically shows a medical connector constructed in accord with preferred embodiments of the invention.

FIG. 1 schematically shows a medical connection device ("connector 10") constructed in accordance with preferred embodiments of the invention. The connector 10 may be any female connection device known in the art for connecting to another fluid transfer device, such as a nozzle, luer, or fluid transfer tube that is connected to a fluid bag. For example, the connector 10 may be a part of a swabbable luer activated valve similar to that shown in copending U.S. patent application entitled, "SWABBABLE LUER-ACTIVATED VALVE," filed on Sep. 13, 1999 and having Ser. No. 09/394,169, the disclosure of which is incorporated herein, in its entirety, by reference. As discussed in greater detail below, the connector disclosed in that patent application acts as a part of a valve for valving fluid transfer between a medical nozzle device (e.g., a luer tip or similar device) and a patient.

The connector 10 includes a connector body 12 with a coupling material 14 (discussed below) for coupling with a nozzle 16. The connector body 12 may be manufactured from any medical grade material such as, for example, polycarbonate or polyester. Among other things, the connector body 12 includes a female proximal opening 18 with an inner periphery 20 for receiving and securing the nozzle 16, a threaded shaft 22 for coupling with mating threads on a threaded skirt (if any) on the nozzle 16, and a lower body portion 24. Of course, as discussed below, the nozzle 16 preferably does not require a threaded skirt or like apparatus to securely couple with the connector 10.

Figure 2:
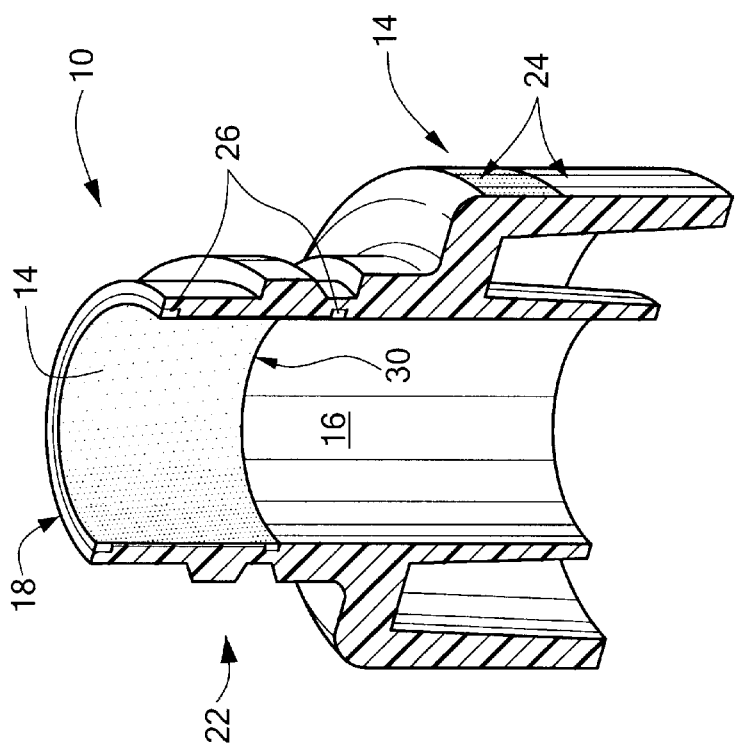
FIG. 2 schematically shows a cut-away view of the medical connector shown in FIG. 1.

In accord with preferred embodiments of the invention, the coupling material 14 is disposed about the inner periphery 20 of the proximal opening 18 for securing the nozzle 16 within the proximal opening 18. In preferred embodiments, the coupling material 14 is a medical grade material, such as rubber or an elastomeric material, having a coefficient of friction that is greater than that of the body. Among other things, the coupling material 14 may be a pre-made material insert that is secured to the inner periphery 20 or, alternatively, material that is molecularly bonded with the inner periphery 20. In either case, the coupling material 14 may be secured to the inner periphery 20 to form a smooth interior surface for coupling with the nozzle 16. As shown in FIG. 2, which shows a cut-away view of the connector 10 shown in FIG. 1, the body includes anchors 26 that secure the coupling material 14 within the connector 10. In alternative embodiments, the interior surface is not smooth.

In preferred embodiments, the coupling material 14 is in the form of a continuous ring of rubber having an inner diameter of about 0.16 inches, an outer diameter of about 0.19 inches, and a longitudinal length of about 0.04 inches. The longitudinal length, material thickness, and coefficient of friction of the coupling material 14 may be modified as necessary, however, to provide optimal nozzle securing functionality.

As suggested above, the inner diameter of the coupling material 14 is selected to approximate that of the nozzle 16 intended for use with the connector 10. In preferred embodiments, the inner diameter is slightly tapered in a manner that is substantially equivalent to that of a standard male luer tip as defined by well known the well known American National Standards Institute (a/k/a ANSI) or International Organization for Standards (a/k/a "ISO") standards. In alternative embodiments, the inner diameter is slightly smaller than that of the nozzle 16. For example, an inner diameter that is smaller than the outer diameter of the nozzle 16 by five percent or less should produce satisfactory nozzle gripping results (depending upon the material used). In preferred embodiments, the inner diameter is between two and five percent smaller than the outer diameter of the nozzle 16. When used within the prior mentioned swabbable valve (i.e., the valve shown in the above noted Ser. No. 09/394,169 patent application) or similar valve, an additional elastomeric valve may be utilized within the connector 10 to valve fluid through the connector 10.

As shown in FIG. 1, coupling material 14 ("outer coupling ring") also may be applied to an outer portion of the lower body portion 24. Any of the noted material configurations shown herein (e.g., a material ring or molecularly bonded material) and other material configurations known in the art may be utilized. This outer coupling ring may be utilized to secure within a female element that circumscribes the connector 10. Although not shown, the nozzle 16 also may have coupling material 14 about its outer periphery to further enhance the connection. In some embodiments, instead of being on the connector 10, the coupling material 14 is disposed about the nozzle 16 only.

Figure 3:
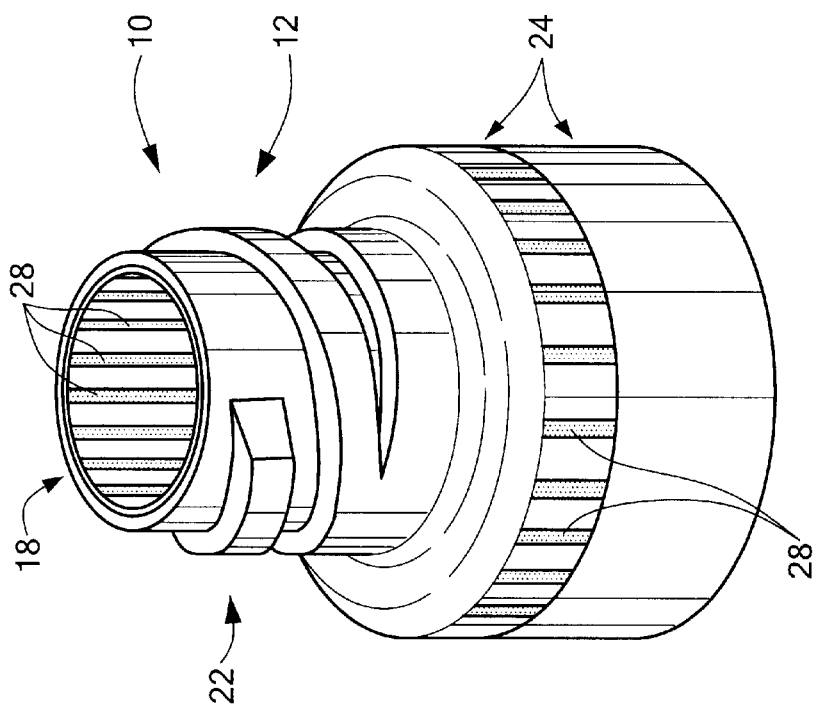
FIG. 3 schematically shows an alternative embodiment of the invention in which the medical connector includes strips of coupling material.

The coupling material 14 also may be in the form of discontinuous coupling material 14 disposed about a part of a nozzle 16 or connector 10. For example, as shown in FIG. 3, the coupling material 14 may be in the form of one or more material strips 28. In other embodiments, the coupling material 14 may be in the form of one or more discontinuous circles, or any other shape. In fact, the coupling material 14 may be in any random location within the inner diameter.

When in use, the nozzle 16 is inserted into the proximal opening 18, consequently causing the coupling material 14 to compress in a radial outward direction. This compression applies a resulting force to the nozzle 16, thus securing the nozzle 16 within the connector 10. A distal end of the coupling material 14 (shown in FIG. 2 at reference number 30) preferably does not move longitudinally and thus, remains secured to its position within the proximal opening 18. Any female parts of the nozzle that are secured over the connector 10 may be secured by means of the outer coupling ring.

In some embodiments, the coupling material 14 may include visual indicium identifying one or more attributes of the connector 10. For example, a set of connectors may be constructed for use with two or more different types of medical procedures. As a further example, a set of connectors may have two or more different proximal opening sizes. A user therefore may distinguish between the different types of connectors by identifying the visual indicium associated with the coupling material 14.

Among other things, the visual indicium may be letters, numbers, various colors, stripes or combinations thereof. Connectors with blue coupling material 14, for example, may be utilized with a first medical procedure, while connectors with green coupling material 14 may be utilized with a second medical procedure. Accordingly, such a set (with blue and green connectors) should enable a user to perform either the first or second medical procedure.

Figure 4:
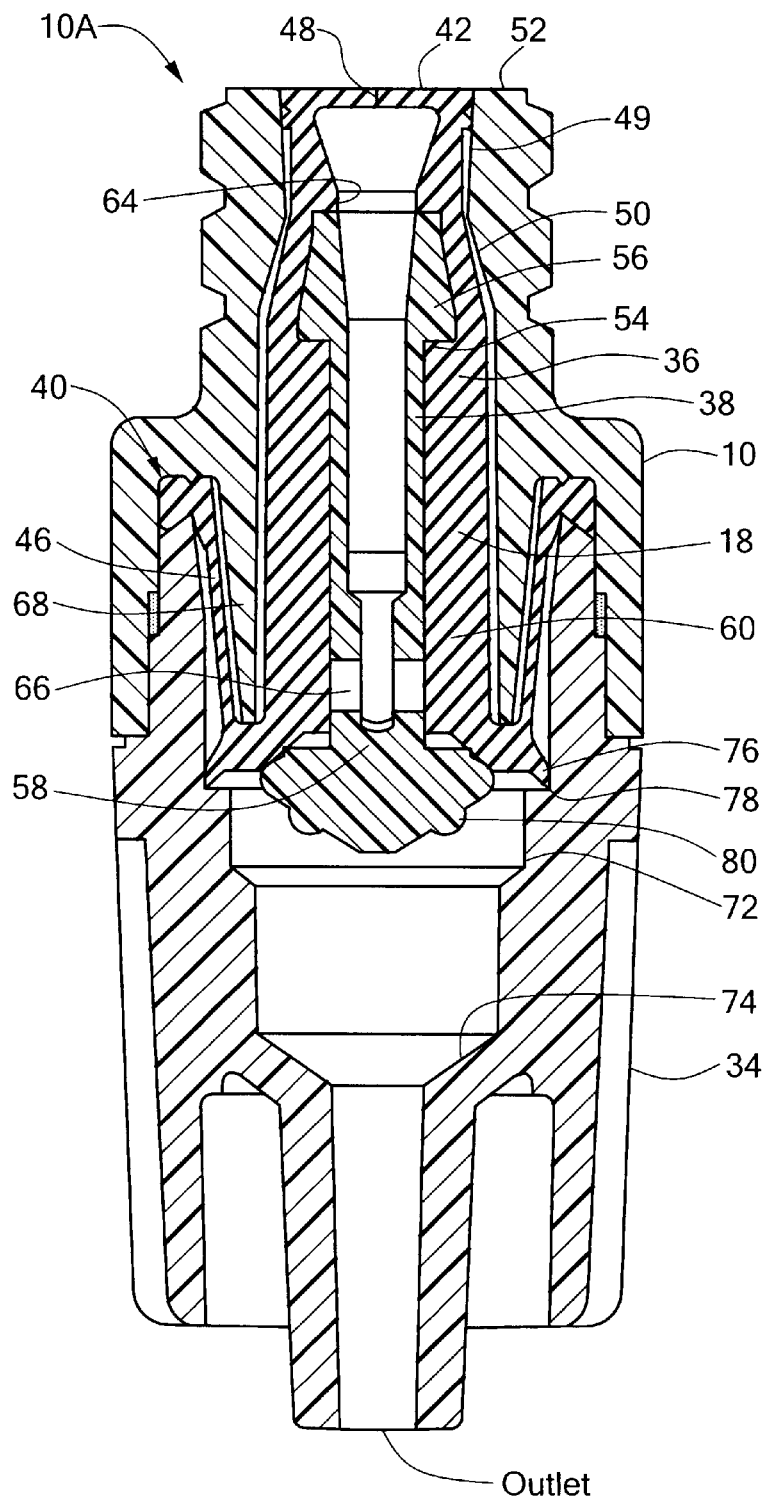
FIG. 4 schematically shows a medical connector constructed in accordance with preferred embodiments of the invention.

FIG. 4 schematically shows a preferred embodiment of the medical connector 10 incorporated into a valve 10A. In particular, the valve 10A includes the connector 10 (described herein as an inlet housing portion 32), an outlet housing portion 34, a gland 36, and a movable, rigid interior cannula 38. The gland 36 and cannula 38 may be considered to form a plunger valve. As known by those skilled in the art, a plunger valve may be any valve that moves longitudinally to valve fluid through a channel (described below). Accordingly, the disclosed gland/cannula plunger valve combination is discussed herein as an example of a preferred embodiment and is not intended to limit other embodiments of the invention.

The two housing portions 32 and 34 preferably are ultrasonically shear welded together to form an integral housing, and to hold one end of the gland 36 in a gland-retention area 40. Fluid passing through the valve 10A passes through the cannula 38, which is located within the gland 36, which in turn is located within the housing. As noted above and shown in FIG. 4, the inlet housing portion 32 includes the opening 18 with the inner periphery 20 and the coupling material 14.

The gland 36, which preferably is manufactured from medical grade silicone, has three primary sections, namely a swabbable seal section 42, a tubular section 44, and an tubular section 46. The seal section 42 has an aperture 48 passing through it that may be, for example, a pierced hole or a slit. When the valve 10A is in a closed mode (i.e., not permitting fluid flow through it), as shown in FIG. 4, the aperture 48 is held closed by both the inner periphery 20 of the housing, and the coupling material 14. Specifically, as discussed above, the inner diameter of the housing at the inlet is smaller than the outer diameter of the seal section 42 of the gland 36, thus causing the housing to squeeze the seal section 42, thereby forcing the aperture 48 closed. This portion of the inlet housing portion 32 is referred to herein as a "compression zone 49."

Farther down the inlet housing passageway is an expansion zone 50 having an inner diameter that is greater than that of the tapered, compression zone 49, and greater than the outer diameter of the seal section 42. Due to this relative geometry, the seal section 42 may expand when it is forced into this zone, thereby permitting the aperture 48 to open. The inlet housing portion 32 also may include a vent (not shown) to ease the movement of the seal section 42 between the expansion zone 50 and the compression zone 49. When the valve 10A is in the fully closed position (as shown in FIG. 4), the seal section 42 is flush with or extends slightly above the exterior inlet face 52 of the housing. The seal section 42 and the exterior inlet face 52 thus present a swabbable surface (i.e., they may be easily wiped clean with some material, such as an alcohol swab).

The tubular section 44 of the gland 36 preferably is designed to be compressible. A support section 54 of the gland 36, located between the seal section 42 and the tubular section 44, may be shaped to match a corresponding ledge 56 on the cannula 38 to hold the top section of the gland 36 in place on the cannula 38.

In addition to the seal section 42 of the gland 36, the valve 10A has a second seal area 60 at the outlet end 58 of the cannula 38. Specifically, the outlet end 58 of the cannula 38 is shaped to provide a seal against the gland 36. The cannula's outlet end 58 has a wider outer diameter than the inner diameter of the compressible, tubular section 44 of the gland 36, and a fluid passageway 64 through the cannula 38 has a transverse channel 66 that redirects the passageway sideways into the gland 36. This arrangement forms a seal when the valve 10A is in the closed position, as shown in FIG. 4, and is able to resist a large amount of back pressure from the outlet end 70 of the valve 10A.

The inlet housing portion 32 also preferably includes a rigid annular extension 68 that separates the gland's tubular section 44 from the gland's tubular section 46. This annular extension 68 ensures that the tubular and attachment sections 44 and 46 of the gland 36 do not fold incorrectly when the valve 10A is opened and closed. In addition, the annular extension 68, in connection with the gland 36, also ensures that the cannula's outlet section 58 does not get forced too far up into the inlet section by a large amount of back pressure. Moreover, the annular extension 68 also prevents the lower portion of the gland 36 from being forced too far up into the inlet section. Since the valve 10A has the second seal area 60 (formed by the cannula's outlet end 58), which is able to resist large back pressures, the first seal (i.e., the aperture 48 through the seal section 42) generally is not required to withstand large proximally directed back pressures.

The gland tubular section 44 preferably is preloaded to normally provide a proximally directed force to the cannula 38. To that end, the gland's tubular section 44 is formed to be sufficiently long with respect to the distance between the cannula's ledge 56 and the cannula's outlet end 58 so that the gland's tubular section 44 is under compression even when the valve 10A is in the closed position. This arrangement improves the effectiveness of the second seal area 60. Specifically, by preloading the gland's tubular section 44, the valve 10A is made more resistant to opening in response to either a positive pressure or a negative pressure applied to the outlet 50. By having a sufficient amount of surface area of the gland 36 exposed to the outlet 50 with respect to the surface area of the cannula 38 exposed to the outlet, the effect on a closed valve of a negative pressure at the outlet will be to pull the gland 36 toward the outlet along with the cannula 38. By having a negative pressure pull both the gland 36 and the cannula 38 toward the outlet, the second seal area 60 remains sealed.

The cannula's outlet end 58 may be made thin enough so that in an emergency, a needle (instead of a luer-taper nozzle) may be used with the valve 10A. The needle may be inserted through the seal section's aperture 48 and the cannula passageway, and then, if the outlet end 58 is made thin enough, the needle may pierce the outlet so that medication may be injected through the valve 10A. The outlet end 58 should be strong enough to resist whatever level of back pressure may be expected from the valve's outlet 70.

The outlet housing portion 34 includes a second ledge 72 to prevent the gland 36 (i.e., the gland's tubular section 46) from extending too far towards the valve's outlet 50. This second ledge 72, however, does not stop the movement of the cannula 38 towards the outlet 50 and thus, the cannula's outlet end 58 may continue to move toward the valve's outlet 50 and telescopically separate from the gland 36. This separation consequently opens the second seal area 60 if it has not yet opened. The outlet housing portion 34 also includes ribs 74 for stopping the movement of the cannula 38 toward the valve's outlet 50, while permitting flow from the cannula 38 between the ribs 74 to the valve's outlet.

The connector 10 also includes a ridge 76 that normally is seated on a third ledge 78 formed by the interior walls of the outlet housing portion 34 This cooperation of the ridge 76 and third ledge 78 provides a proximal biasing force to the gland 36. In addition, the cannula outlet end 58 also may include cannula ribs 80 for limiting longitudinal motion of the cannula 38 toward the outlet end 70 of the valve 10A. Accordingly, in some embodiments, there is no need for ribs 74 to protrude from the interior walls of the outlet housing portion 34.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

We claim:

1. A medical coupling device comprising:
   a housing, the housing manufactured from a housing material, the housing material having a housing material frictional value;
   a proximal fluid port for receiving a male nozzle, the proximal fluid port defined by the housing and having an inner periphery;
   a plunger valve for valving fluid flow through the proximal fluid port;
   a coupling material fixedly disposed about the inner periphery of the fluid port to form a smooth interior surface;
   the coupling material and inner periphery forming an opening having an opening inner diameter that receives the plunger valve, the opening inner diameter sized to receive and secure the male nozzle, the plunger valve normally closing the opening inner diameter when the nozzle and the device are in an uncoupled position, the nozzle closing the opening diameter and contacting the interior surface of the coupling material when the nozzle and the device are in a coupled position.

2. The medical coupling device as defined by claim 1, wherein the plunger valve includes a movable, rigid member that moves longitudinally to valve fluid through a channel.

3. The medical coupling device as defined by claim 1 wherein the plunger valve includes a rigid cannula.

4. The medical coupling device as defined by claim 3 wherein the plunger valve comprises a gland that normally biases the rigid cannula proximally.

5. A medical coupling device comprising:
- a housing manufactured from a housing material, the housing material having a housing material frictional value;
- a proximal fluid port for receiving a male nozzle with a nozzle outer diameter, the proximal fluid port defined by the housing and having an inner periphery;
- a plunger valve for valving fluid flow through the proximal fluid port;
- a coupling material having a coupling material frictional value that is greater than the housing material frictional value,
- the coupling material being fixedly disposed about the inner periphery of the fluid port to form a smooth interior surface,
- the coupling material and inner periphery forming an opening having an opening inner diameter that receives the plunger valve, the opening inner diameter sized to receive and secure the male nozzle, the plunger valve normally closing the opening inner diameter when the nozzle and the device are in an uncoupled position,
- the nozzle remaining proximal to the plunger valve and closing the opening inner diameter when the nozzle is received in the proximal fluid port, the coupling material securing the nozzle by contacting the nozzle.

6. The medical coupling device as defined by claim 5 wherein the coupling material comprises elastomeric material.

7. The medical coupling device as defined by claim 5 wherein the proximal fluid port comprises a proximal surface, the plunger valve being substantially flush with the proximal fluid port to form a swab valve.

8. The medical coupling device as defined by claim 5, wherein the plunger valve includes a movable, rigid member that moves longitudinally to valve fluid through a channel.

9. The medical coupling device as defined by claim 5 wherein the plunger valve includes a rigid cannula.

10. The medical coupling device as defined by claim 9 wherein the plunger valve comprises a gland that normally biases the rigid cannula proximally.

11. The medical coupling device as defined by claim 5 further comprising an exterior surface, the exterior surface having exterior coupling material disposed thereon.

12. The medical coupling device as defined by claim 11 wherein the exterior coupling material includes indicia identifying an attribute of the medical coupling device.

* * * * *